(12) United States Patent
Mendius et al.

(10) Patent No.: US 6,605,108 B2
(45) Date of Patent: Aug. 12, 2003

(54) MONOCANALICULAR STENT

(75) Inventors: Richard W. Mendius, Collierville, TN (US); James S. Linder, Memphis, TN (US)

(73) Assignee: Eagle Vision, Inc., Memphis, TN (US)

( * ) Notice: Subject to any disclaimer, the term of this patent is extended or adjusted under 35 U.S.C. 154(b) by 132 days.

(21) Appl. No.: 09/834,540

(22) Filed: Apr. 13, 2001

(65) Prior Publication Data

US 2002/0151960 A1 Oct. 17, 2002

(51) Int. Cl.$^7$ ............................................... A61M 29/00
(52) U.S. Cl. ........................................ 623/1.11; 604/8
(58) Field of Search .................. 604/8; 623/1.11–1.12, 623/4.1

(56) References Cited

U.S. PATENT DOCUMENTS

| | | | |
|---|---|---|---|
| 3,726,284 A | | 4/1973 | Parker .................... 128/350 R |
| 4,305,395 A | * | 12/1981 | Martinez ...................... 604/28 |
| 5,318,513 A | * | 6/1994 | Leib et al. ...................... 604/8 |
| 5,417,651 A | | 5/1995 | Guena .............................. 604/8 |
| 5,423,777 A | * | 6/1995 | Tajiri et al. .................. 604/294 |
| 5,993,407 A | | 11/1999 | Moazed .......................... 604/8 |
| 6,041,785 A | * | 3/2000 | Webb .......................... 128/887 |
| 6,238,363 B1 | | 5/2001 | Kurihashi ...................... 604/8 |
| 6,383,192 B1 | | 5/2002 | Kurihashi ................... 606/108 |

FOREIGN PATENT DOCUMENTS

| | | | |
|---|---|---|---|
| EP | 0 988 844 A2 | * | 3/2000 |

OTHER PUBLICATIONS

EagleVision physician instruction pamphlet on the EV Monocanalicular stent, 1989, 2 pages.
EagleVision physician instruction pamphlet on the EV Monocanalicular stent, 1991, 2 pages.
EagleVision physician instruction pamphlet on the EV Monocanalicular stent, 1992, 2 pages.
EagleVision product description on the EV Monocanalicular stent, 1997, 1 page.
Internet article on Ocular Surgery News—on the Monocanalicular stent used to dilate stenotic punctum, 3 pages, Jan. 15, 2001.
Product page including Mini Monoka, for canalicular lacerations, 1 page.

* cited by examiner

Primary Examiner—Corrine McDermott
Assistant Examiner—Thomas J Sweet
(74) Attorney, Agent, or Firm—Gordon & Jacobson, P.C.

(57) ABSTRACT

A monocanalicular stent includes a plug and a tubing molded with or coupled to the plug portion at an angle. The plug portion preferably includes a body portion, a neck portion, and a head portion. The tubing extends substantially longer than the plug portion. A delivery stylet is also provided and extends into a pathway of the tubing and provides a device by which the physician may handle the stent and insert it into the canaliculus. The tubing portion may be cut to length and closed. The stylet is then maneuvered to deliver the stent into a dilated punctal opening and then advanced through the canaliculus until the position of the plug portion is immediately above the punctal opening. The stylet is then removed, and the plug portion is then manipulated into the punctal opening until the head portion is flush with the surface of the punctal opening.

30 Claims, 4 Drawing Sheets

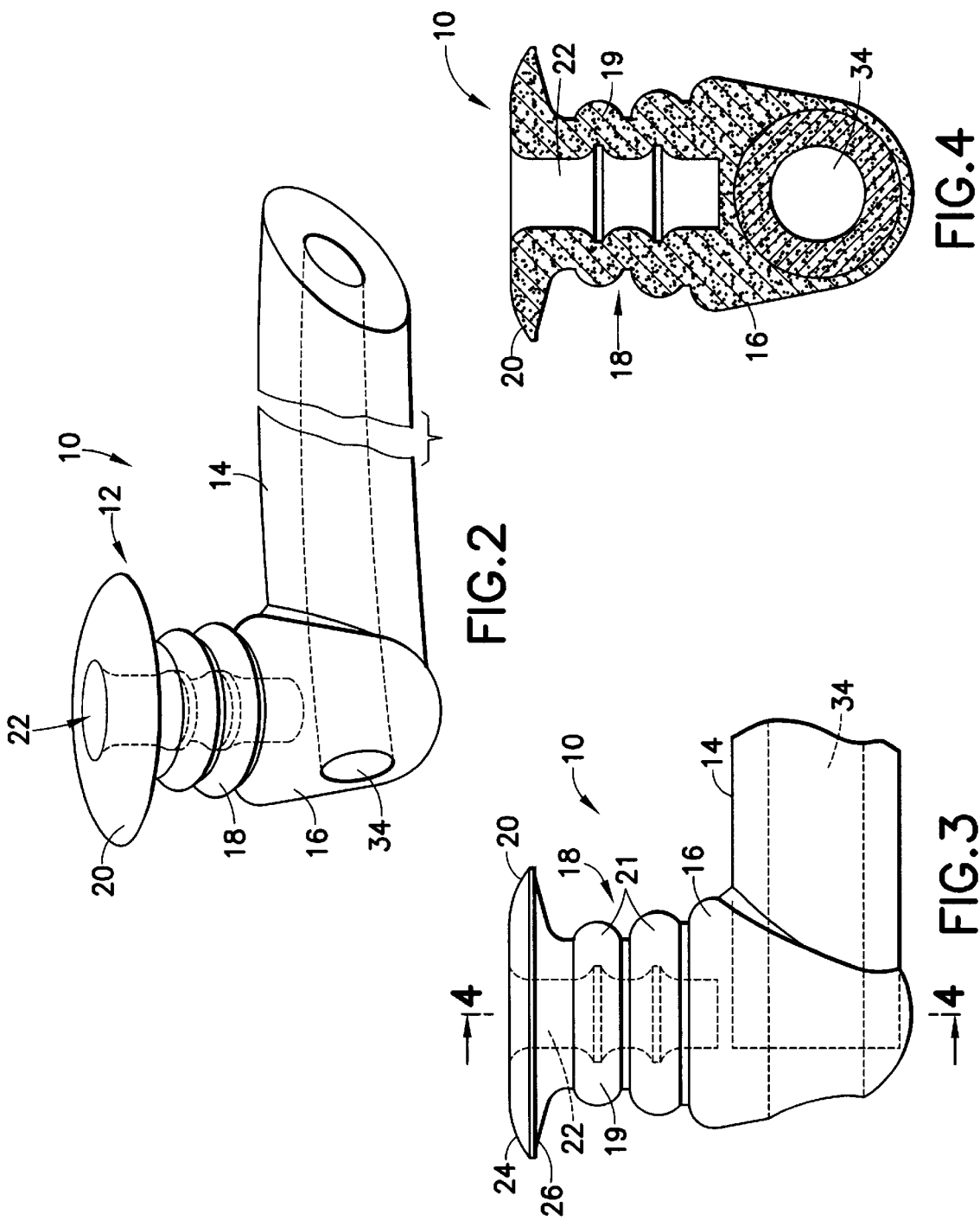

MONOCANALICULAR STENT

BACKGROUND OF THE INVENTION

1. Field of the Invention

This invention relates broadly to medical devices. More particularly, this invention relates to canalicular implants for use in the repair of a damaged or malformed lacrimal canaliculi.

2. State of the Art

The lacrimal canaliculus is the canal leading from the lacrimal punctum to the lacrimal sac which empties into the nose. The canaliculus can become lacerated as a result of injury. One common cause of this type of injury, particularly in children, is a scratch from an animal claw in the proximity of the eye. Other common causes of canalicular damage requiring reconstruction include car accidents, cancer, and canalicular stenosis.

Additionally, there is a condition in which there is a lack of fluid communication between the lacrimal sac and the nasal cavity. Such a condition is treated with a dacryosystorhinostomy (DCR) in which a new tear drainage channel is surgically constructed between the lacrimal sac and the nasal cavity. Furthermore, pediatric congenital nasolacrimal duct obstructions can occur in which the nasolacrimal duct does not fully form and open within a normal time frame, e.g., one year, after birth, and must be surgically opened. In both these situations, after reconstruction of or opening of the passageway it is desirable to maintain the passageway in the open configuration during healing such that after healing patency is provided.

SUMMARY OF THE INVENTION

It is therefore an object of the invention to provide a monocanalicular stent which can be temporarily inserted into the canaliculus and, if desired, into the nasolacrimal duct to aid in repair and healing of a lacerated, constructed, or opened canaliculus.

It is another object of the invention to provide a monocanalicular stent which provides a structure about which canalicular or nasolacrimal duct tissue can heal.

It is a further object of the invention to provide a monocanalicular stent which permits surrounding tissue to heal in a manner which after healing provides an open channel for drainage of fluid from the lacrimal sac into the nose.

It is also an object of the invention to provide a monocanalicular stent which can be relatively easily inserted by a physician into the nasolacrimal duct.

It is an additional object of the invention to provide a monocanalicular stent which is customizable in length by a physician depending upon the application and the anatomy.

In accord with these objects, which will be discussed in detail below, a monocanalicular stent is provided which includes a plug portion and an elongate tubing portion preferably molded with or coupled to the plug portion at approximately a ninety-degree angle.

The plug portion preferably includes a body portion, a neck portion, and a head portion, and an axial bore partially extending therein. The neck portion preferably includes an accordion-like construction, permitting the neck portion to bend, stretch, and collapse as necessary to maintain an anatomical fit at the vertical punctum. The head portion is preferably designed to have a low profile at the punctal opening.

The leading end of the tubing portion is preferably cut at an angle to create a leading surface which facilitates insertion of the stent into the nasolacrimal duct. The tubing portion extends substantially longer than the plug portion; for example, twenty times the length or more. According to a preferred embodiment, the tubing portion includes a pathway which extends the entire length thereof. According to another embodiment of the invention, the pathway of the tubing portion and the bore of the plug portion are in communication.

A delivery stylet is also provided and extends into the tubing pathway (and bore of the plug portion where such is in communication with the tubing pathway) and provides a tool by which the physician may handle the stent and insert it into the canaliculus or nasolacrimal duct.

Prior to use, the stent is cut to length, as necessary, and the leading end of the stent is tied closed with a suture. The stylet is then maneuvered to deliver the stent into a dilated punctal opening. The stent is then advanced through the canaliculus until the position of the plug portion is immediately above the punctal opening. The stylet is removed, and the plug portion is then manipulated into the punctal opening until the rim of the head portion is flush with the surface of the punctal opening.

Additional objects and advantages of the invention will become apparent to those skilled in the art upon reference to the detailed description taken in conjunction with the provided figures.

BRIEF DESCRIPTION OF THE DRAWINGS

FIG. 2 is a transparent broken perspective view of the first embodiment of the monocanalicular stent according to the invention;

FIG. 3 is a transparent broken side elevation view of the first embodiment of the monocanalicular stent according to the invention;

FIG. 4 is a section view across line 4—4 in FIG. 3;

DETAILED DESCRIPTION OF THE PREFERRED EMBODIMENTS

Figure 1:
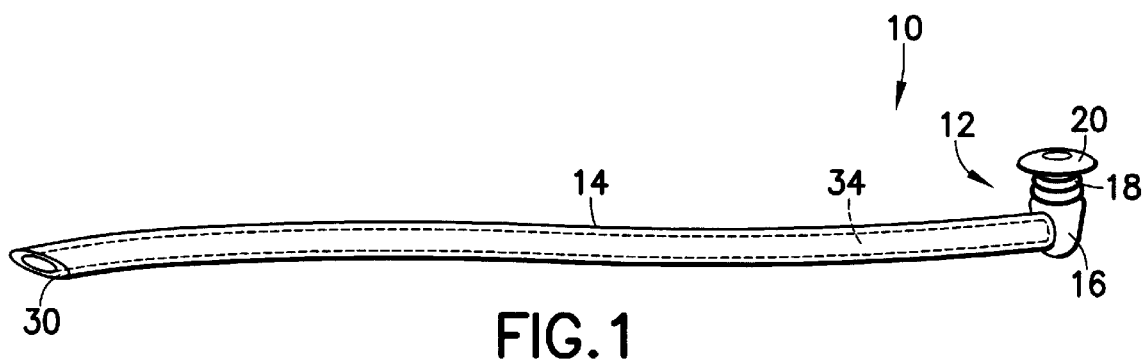
FIG. 1 is a perspective view of a first embodiment of the monocanalicular stent according to the invention.

As used herein, the term 'proximal' refers to a location relatively closer to a hand of a physician inserting the monocanalicular stent into a patient, and the term 'distal' refers to a location relatively further from the hand of the physician, particularly during insertion of the stent into the patient.

Turning now to FIGS. 1 through 4, a monocanalicular stent 10 according to a first embodiment of the invention is shown. The stent 10 includes a proximal plug 12 and an elongate distal tubing 14 molded with or coupled to the plug at preferably approximately a ninety-degree angle relative to a longitudinal axis of the plug. The stent 10 is preferably made from silicone, but may be made from another suitable flexible biocompatible material.

The plug 12 preferably includes a body portion 16, a neck portion 18, and a head portion 20, and preferably an axial bore 22 extending at least partially into the head and neck portions. The body portion 16 is preferably substantially conical or frustoconical in shape. The neck portion 18 has a wall 19 with a preferably accordion-like construction, providing the wall with a plurality of undulations 21 and permitting the neck portion to bend, collapse, and stretch. This construction is described in detail in U.S. Pat. No. 6,041,785 which is hereby incorporated by reference herein in its entirety. In view of the preferred configuration of the neck portion, it will be appreciated that the axial bore 22 within the wall 19 has various diameters along its length. In addition, the neck portion is tapered toward the head portion. The various structural elements of the neck portion enable the neck portion to be extremely flexible and compliant and facilitate bending of the neck portion within the vertical punctal without further irritation to the already damaged tissue. The head portion 20 is preferably configured perpendicular to an axis of the plug and is designed to have a low profile at the punctal opening, as described in U.S. Pat. No. 6,027,470, which is also hereby incorporated by reference herein in its entirety. In brief, the upper surface 24 and lower surface 26 of the head portion 20 are tapered toward the periphery of the head portion. All portions of the plug 12 are so configured as to provide a good anatomical fit in the vertical punctum.

The tubing 14 includes a leading end (or free end) 30 which is preferably at an oblique angle, and more preferably at an acute angle, relative to the axis of the tubing to create an angled leading surface 32 which facilitates insertion of the stent 10 into the nasolacrimal duct. In accord with the first embodiment, a longitudinal pathway 34 is provided completely through the tubing 14 and the body portion 16 of the plug 12, and is preferably not in communication with the axial bore 22 of the plug 12. The longitudinal pathway 34 is preferably oriented substantially ninety degrees relative to the axial bore 22. The tubing 14 extends substantially longer than the plug 12; for example, approximately twenty times the length or more. For purposes of example, and not by way of limitation, the following dimensions are provided for one size of the stent: a plug length of approximately 2.5 mm, a tubing length of approximately 50 mm, a tubing diameter of approximately 0.94 mm, and a longitudinal pathway diameter of approximately 0.51 mm. Other tubing lengths, preferably between 10 mm and 50 mm may also be used.

Figure 5:
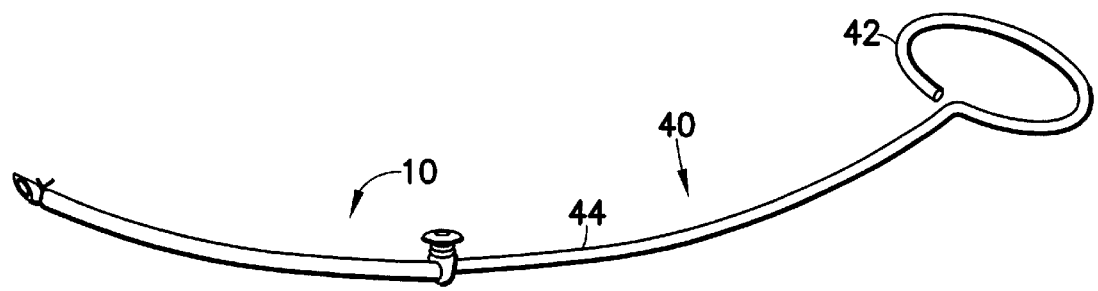
FIG. 5 is a perspective view of the first embodiment of the monocanalicular stent mounted on a preferably malleable delivery stylet according to the invention.

Referring now to FIG. 5, a delivery stylet 40 is also provided and extends into the longitudinal pathway 34. The stylet 40 is a preferably malleable, preferably stainless steel device by which the physician may handle the stent 10 and insert it into the nasocrimal duct. The stylet 40 preferably includes a looped handle portion 42, and a stent delivery portion 44 which is sized to fit within the longitudinal pathway 34 and extend to adjacent the free end 30 of the tubing 14. The stent delivery portion 44 may be provided with a gentle curve, or otherwise bent or customized by the physician prior to use, in order to facilitate insertion of the stent 10.

Figure 6:
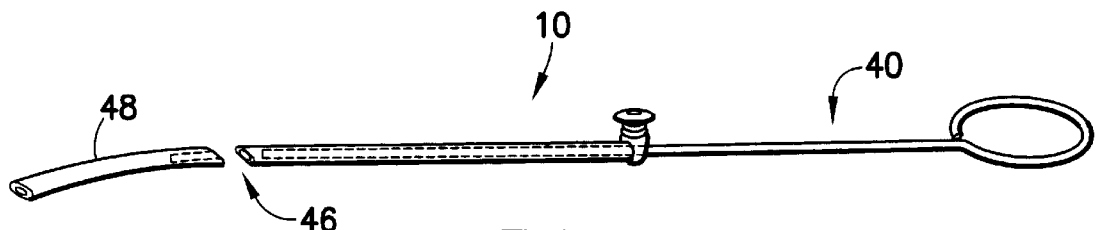
FIGS. 6 through 9 illustrate a method according to the invention of inserting the monocanalicular stent into the nasolacrimal duct.
Figure 7:
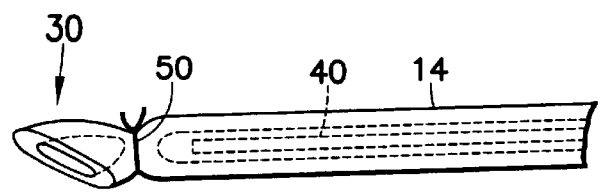

The stent 10 is adapted to provide a structure about which a canaliculus can heal after injury or surgical construction or reconstruction. Prior to use, it may be desirable to cut the tubing 14 of the stent 10 to a shorter length. If so, the stylet 40 is first partially withdrawn from the longitudinal pathway 34 so as not to interfere when the tubing 14 is cut. Referring to FIG. 6, the cut 46 is preferably made along the same oblique angle as previously provided so as to maintain the leading surface configuration at the leading end 30 and thereby permit a more efficient insertion. The excess tubing 48 is cut free and discarded. Turning to FIG. 7, whether or not the tubing 14 is cut to a shorter length, the leading end 30 is tied closed, preferably with an absorbable 6-0 suture 50 to prevent the stylet 40 from extending beyond the leading end 30 during insertion. The stylet 40 is then advanced to the closed end of the tubing 14. Optionally, an ophthalmic ointment is applied to the tubing 14 immediately prior to insertion.

Figure 8:
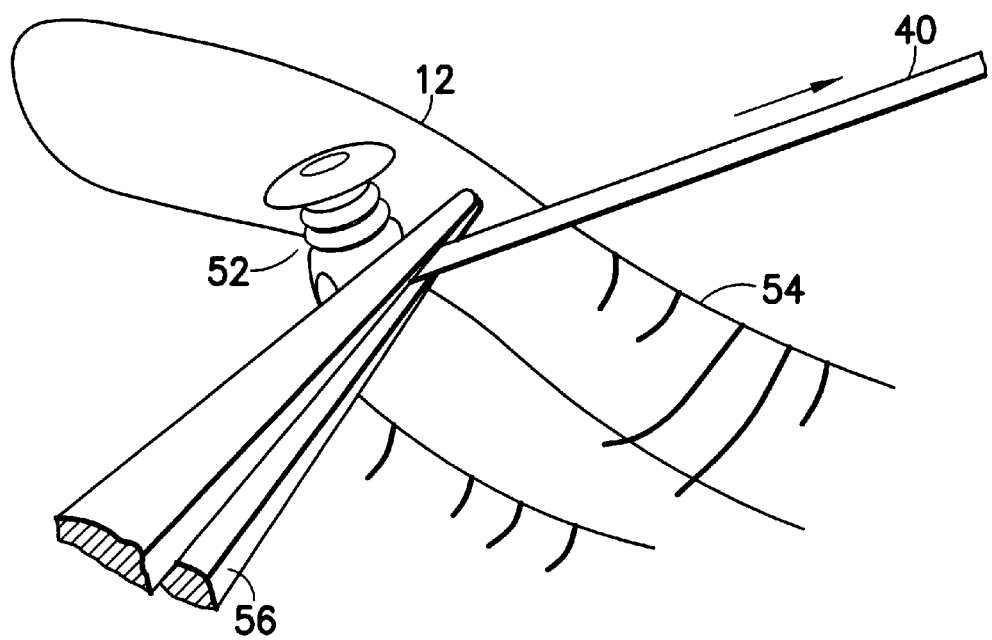
Figure 9:
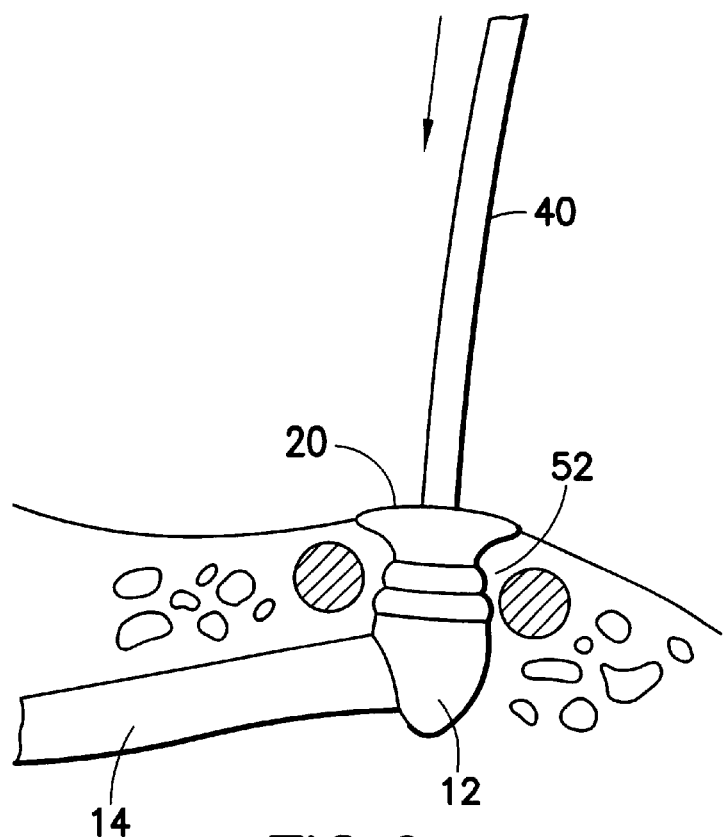

The punctum is then dilated with a tapered probe to a sufficient diameter to facilitate insertion of the stent 10. The stylet is manipulated to thread the stent 10 into the punctal opening and advance the tubing 14 of the stent 10 through the locus of the canaliculus damage or repair, and until the position of the plug 12 is immediately above the punctal opening 52 near the lower lid 54 of the eye. Referring to FIG. 8, the stylet is then removed, e.g., by using a forceps 56 as a stop against the plug 12 while gently withdrawing the stylet 40.

After the stylet 40 is removed, either the end of the stylet, the tip of a forceps, or another tool is used to manipulate or nudge the remainder of the stent, i.e., the plug 12, into the punctal opening 52. The plug 12 is properly seated when the underside of the head portion 20 is flush with the surface of the punctal opening. It is common in the prior art to access and pull a portion of the stent through the nose in order to fully seat such stent. However, with the stent of the invention, there is never a need to access the tubing of the stent of the invention through the nose in order to fully insert the stent, as the stent is stiff on the stylet during insertion. In addition, it is not necessary to secure the plug portion with sutures. Furthermore, it will be appreciated that because the leading end 30 of the tubing 14 is closed, the stent 10 does not provide a fluid pathway through the nasolacrimal duct; however, the fluid may pass along the outside of the stent. The stent 10 remains in the canaliculus until the canaliculus is sufficiently healed. In a damaged or stenotic lacrimal drainage system, the stent provides a structure about which the tissue can heal such that upon removal a well-defined lacrimal drainage pathway is provided. After a dacryosystorhinostomy (DCR), the stent helps form a drainage channel from the lacrimal sac into the nose. Once the tissue has properly healed about the stent, the stent 10 is removed by gently grasping the plug portion under the head 20 of the plug 12, e.g., with a forceps, and withdrawing the stent from the canaliculus.

As briefly discussed above, an important aspect of the stent of the invention is that it is stiff during insertion into the canaliculus (as a result of the delivery stylet within), and after insertion is substantially soft and flexible. This temporary stiffness permits the stent to be maneuverable and facilitates insertion of the stent through bends in the anatomy through which a flexible stent would be otherwise unable to traverse. For example, the corner at the top of the lacrimal sac and the opening at the lower part of the nasolacrimal duct can be traversed by the stent on the delivery stylet, but not by a flexible stent alone. After removal of the delivery stylet, the flexible stent, having the structural advantages previously discussed, provides excellent patient tolerance.

Figure 11:
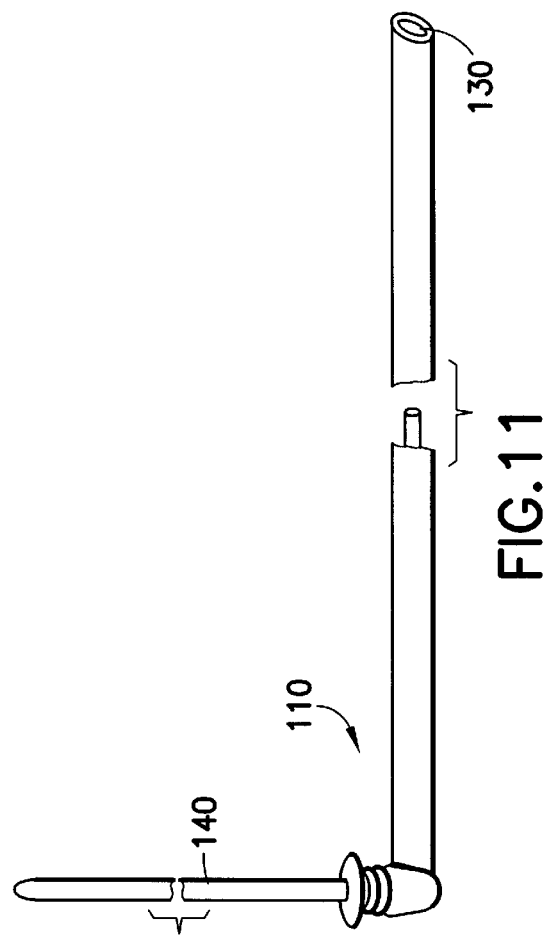
FIG. 11 is a broken perspective view of the second embodiment of the monocanalicular stent mounted on a provided stylet according to the invention.
Figure 10:
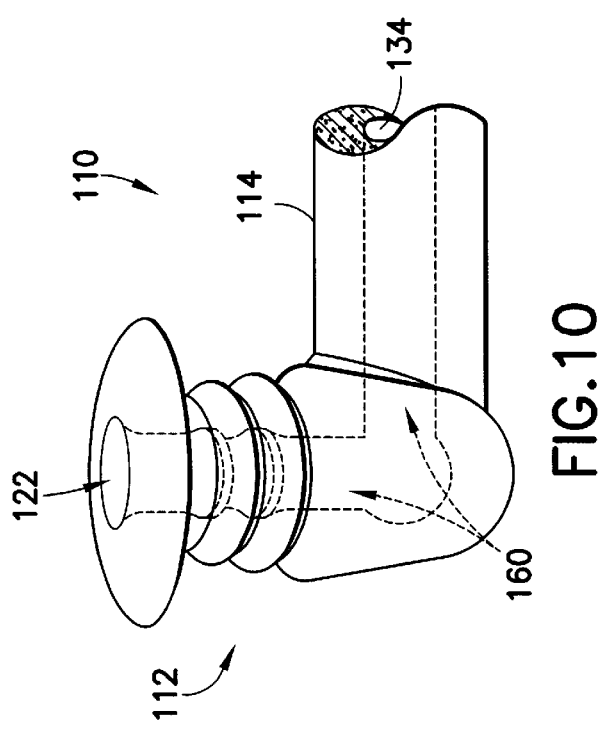
FIG. 10 is a transparent broken perspective view of a second embodiment of a monocanalicular stent provided on a delivery stylet according to the invention.
Figure 12:
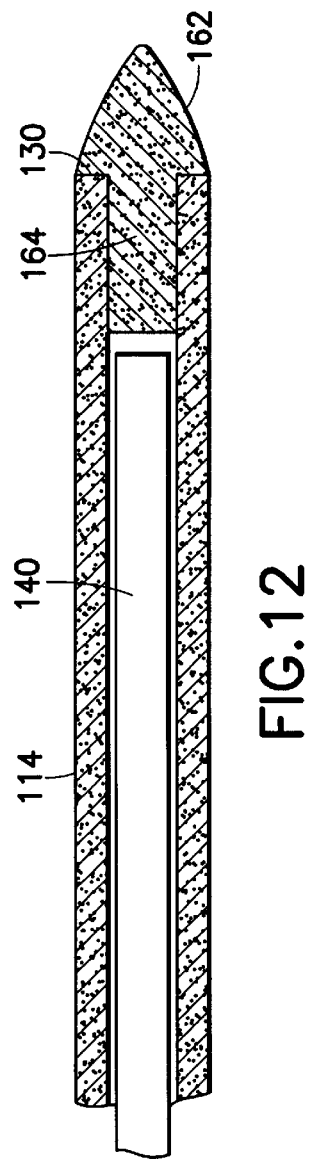
FIG. 12 is a broken longitudinal section view of a distal portion of the tubing of a monocanalicular stent according to the invention showing an alternative means by which to close the end of the tubing.

Referring now to FIG. 10, a second embodiment of a monocanalicular stent 110, substantially similar to the first embodiment (with like elements having numbers incremented by 100), is shown. According to the second embodiment, the axial bore 122 of the plug 112 and the longitudinal pathway 134 through the tubing 114 are in communication and define an L-shaped pathway 160. In contrast to the first embodiment, the longitudinal pathway 134 preferably does not exit through the body portion 120 of the plug 112. Referring to FIG. 11, the stent 110 is preferably provided on an L-shaped stylet 140, with the stylet extending through the L-shaped pathway 134 of the stent. Prior to use, the stent is preferably moved distally along the stylet such that the stent is located entirely on the relatively longer portion of the L-shaped stylet, and the shorter portion and a section of the longer portion then function as a handle for the physician. The stent 110 also preferably includes a leading end 130 cut at an acute angle to facilitate insertion. According to an alternate embodiment, suitable for either of the first or second embodiment, the leading end 130 may be cut transverse the axis of the tubing and a preferably conical nose piece 162, made e.g. of collagen, with a reduced diameter tubular proximal portion 164 which may be snugly fit into the end 130 of the tubing 114 and thereby facilitate insertion (FIG. 12). In such a case, it will be appreciated that the leading end 130 of tubing 114 is not necessarily tied closed with suture, as the tubing is swaged onto the nosepiece, but that a suture may be used to secure the nose piece 162 at the leading end 130. Moreover, where a preformed L-shaped stylet 140 is used, the stylet is partially withdrawn so that the end may be closed a the appropriate length, and the stylet does not extend beyond the tubing, as previously described.

There have been described and illustrated herein several embodiments of a monocanalicular stent and a method of inserting the same into a damaged or repaired canaliculus to facilitate healing of the canaliculus or nasolacrimal duct. While particular embodiments of the invention have been described, it is not intended that the invention be limited thereto, as it is intended that the invention be as broad in scope as the art will allow and that the specification be read likewise. Thus, while it is preferred that the tubing be oriented substantially ninety degrees relative to the plug for purposes of anatomical fit, it will be appreciated that other angles may be used as well. For example, where the plug is of a more extended shape and can flex or is formed with its distal end at an angle relative to the proximal end, the tubing can be oriented at a smaller angle (or at no angle) relative to the distal end of the plug, although the tubing will still be at an angle of substantially ninety degrees relative to the proximal end of the plug. In addition, while the neck of the plug preferably has an accordion-like configuration, it will be appreciated that other neck configurations, including a relatively smooth shaped exterior may be used. Also, while the head is preferably designed to have a low profile upon implantation, it will be appreciated that other head designs may be used. Further, while it has been disclosed that the leading end of the tubing be closed with suture or a nose element, it will be understood that other means for closing the end sufficient to resist the end of the stylet from passing therethrough during insertion can be used. For example, the leading end can be heat sealed. Furthermore, while particular stylets have been disclosed, including a stylet with a preformed L-shaped bend, it will be appreciated that stylets can be bent to whatever shape the physician desires and made from materials other than stainless steel. Moreover, while the leading end of the tubing is described as having a closed end, it will be appreciated that the leading end need not be closed if a sufficiently tight fit is provided between the stylet and the tubing. It will therefore be appreciated by those skilled in the art that yet other modifications could be made to the provided invention without deviating from its spirit and scope as claimed.

What is claimed is:

1. A monocanalicular stent for insertion into a canaliculus of a nasolacrimal duct of a human, comprising:
   a) a plug portion having proximal portion defining an axis and a distal portion; and
   b) a tubular portion having a proximal end integral with said distal portion of said plug portion and a distal end, said tubular portion defining a longitudinal axis which is angled relative to said axis defined by said proximal portion of said plug portion, said tubular portion being sized to fit within the canaliculus,
   wherein a longitudinal pathway parallel with said longitudinal axis of said tubular portion extends through said tubular portion and out of an opening in said plug portion which is oriented non-axially relative to said axis of said plug portion.

2. A monocanalicular stent according to claim 1, wherein:
   said plug portion includes an axial bore partially extending therethrough.

3. A monocanalicular stent according to claim 2, wherein:
   said axial bore and longitudinal pathway are not in communication.

4. A monocanalicular stent according to claim 1, wherein:
   said distal end of said tubular portion is oblique relative to said longitudinal axis.

5. A monocanalicular stent according to claim 1, wherein:
   said plug portion has a first length, and said tubing portion has a second length at least approximately four times said first length.

6. A monocanalicular stent according to claim 1, wherein:
   said plug portion has a first length, and said tubing portion has a second length at least approximately ten times said first length.

7. A monocanalicular stent according to claim 1, wherein:
   said distal end of said tubular portion is closed.

8. A monocanalicular stent according to claim 1, wherein:
   said distal end of said tubular portion is closed with a suture.

9. A monocanalicular stent according to claim 1, wherein:
   said distal end of said tubular portion is closed with a conical nosepiece.

10. A monocanalicular stent according to claim 1, wherein:
    said plug portion includes a proximal head portion, a distal body portion, and a neck portion between head and body portions, said neck portion having a wall with an accordion-like configuration.

11. A monocanalicular stent according to claim 1, wherein:
    said plug portion includes a proximal head portion, a distal body portion, and a neck portion between said head portion and said body portion, said neck portion having a structure adapted to bend, collapse, and stretch.

12. A monocanalicular stent according to claim 1, wherein:
    said plug portion includes a proximal head portion, a distal body portion, and a neck portion between said head portion and said body portion, and wherein said neck portion includes a wall provided with a plurality of undulations.

13. A monocanalicular stent according to claim 1, wherein:
said plug portion includes a proximal head portion, a distal body portion, and a neck portion between said head portion and said body portion, and
wherein said neck portion tapers toward said head portion.

14. A monocanalicular stent according to claim 1, wherein:
said plug portion includes a proximal head portion, a distal body portion, and a neck portion between said head portion and said body portion, and
wherein said head portion includes upper and lower surface which taper toward a periphery of said head portion.

15. A monocanalicular stent according to claim 1, wherein:
said plug portion includes a proximal head portion with a topmost surface, a distal body portion, and a neck portion between said head portion and said body portion, and
wherein said topmost surface of said head portion of said plug portion is oriented substantially perpendicular relative to said axis of said plug portion.

16. A monocanalicular stent according to claim 1, further comprising:
c) a delivery element having a stent delivery portion extending into said longitudinal pathway, and a handle portion external to said longitudinal pathway which is manipulable by a physician, said delivery element being removable from within said longitudinal pathway.

17. A monocanalicular stent for insertion into a canaliculus of a nasolacrimal duct of a human, comprising:
a) a plug portion having a proximal portion defining an axis and a distal portion;
b) a tubular portion having a proximal end integral with said distal portion of said plug portion and a distal end, said tubular portion defining a longitudinal axis which is angled relative to said axis defined by said proximal portion of said plug portion, said tubular portion being sized to fit within the canaliculus,
wherein a pathway is defined coaxial with said axis of plug portion and said longitudinal axis of said tubular portion, and
wherein said tubular portion has a length which is at least approximately ten times a length of said plug portion; and
c) a delivery element having a stent delivery portion extending through said pathway in said plug portion and said tubular portion, and a handle portion external said pathway which is manipulable by a physician, said delivery element being removable from within said pathway.

18. A monocanalicular stent according to claim 17, wherein:
said plug portion includes a proximal head portion, a distal body portion, and a neck portion between said head portion and said body portion, said neck portion having a structure adapted to bend, collapse, and stretch.

19. A monocanalicular stent according to claim 17, wherein:

said plug portion includes a proximal head portion, a distal body portion, and a neck portion between said head portion and said body portion, and
wherein said neck portion is tapered toward said head portion.

20. A monocanalicular stent according to claim 17, wherein:
said plug portion includes a proximal head portion, a distal body portion, and a neck portion between said head portion and said body portion, and
wherein said head portion includes upper and lower surfaces tapered toward a periphery of said head portion.

21. A monocanalicular stent according to claim 17, wherein:
said distal end of said tubular portion is closed.

22. A monocanalicular stent according to claim 17, wherein:
said pathway is substantially L-shaped.

23. A monocanalicular stent system for use by a physician in a canaliculus of a nasolacrimal duct of a human, comprising:
a) an L-shaped monocanalicular stent having a plug portion and a tubular portion angled relative to said plug portion, said tubular portion being sized to fit within the canaliculus,
wherein a pathway is defined through said tubular portion and a portion of said plug portion, said pathway having a first portion within said tubular portion and a second portion within said plug portion; and
b) a delivery element having a stent delivery portion extending into both of said first and second portions of said pathway, and a handle portion external said pathway which is manipulable by the physician, said delivery element being removable from within said longitudinal pathway.

24. A monocanalicular stent system according to claim 23, wherein:
said delivery element is made of metal.

25. A monocanalicular stent system according to claim 23, wherein:
said stent is made of silicone.

26. A method for inserting a stent into a canaliculus of a nasolacrimal duct which is injured or in need of repair, the nasolacrimal duct defining a pathway from the punctum adjacent the eye to the nose, comprising:
a) providing a delivery device having a stent thereon, the stent having a plug portion and a tube portion angled relative to said plug portion, the tube portion having a proximal end coupled to the plug portion and a leading end which is closed, the stent having a pathway extending through the plug portion and the tube portion, and the delivery device extending through the pathway through the plug portion and into the tube portion;
b) maneuvering the delivery device to insert the leading end of the tube portion into the punctum;
c) manipulating the delivery device to push the tube portion into the canaliculus such that the tube portion extends across the locus of injury or repair and the plug portion is seated in the punctum; and
d) withdrawing the delivery device from stent.

27. A method according to claim 26, further comprising:
e) pushing the plug portion of the delivery device into the punctum.

28. A method according to claim 26, further comprising:
e) prior to maneuvering the delivery device to insert the leading end into the punctum, cutting the tube portion to a shorter length and closing the tube.

29. A method according to claim 28, wherein:
said tube portion is tied closed.

30. A method according to claim 26, further comprising:
e) prior to maneuvering the delivery device to insert the leading end into the punctum, applying an ophthalmic ointment to the tubing.

* * * * *